(12) United States Patent
Dambra et al.

(10) Patent No.: US 10,002,678 B2
(45) Date of Patent: Jun. 19, 2018

(54) REDUNDANT ERROR DETECTION IN A CLINICAL DIAGNOSTIC ANALYZER

(71) Applicant: Ortho-Clinical Diagnostics, Inc., Raritan, NJ (US)

(72) Inventors: Joseph J. Dambra, Rochester, NY (US); Jean-Christophe Hurpeau, Saint-Amoult-en-Yvelines (FR); Mark D. Reed, Honeoye Falls, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 131 days.

(21) Appl. No.: 15/045,852

(22) Filed: Feb. 17, 2016

(65) Prior Publication Data

US 2016/0162653 A1 Jun. 9, 2016

Related U.S. Application Data

(63) Continuation of application No. 12/493,689, filed on Jun. 29, 2009, now abandoned.

(60) Provisional application No. 61/077,245, filed on Jul. 1, 2008.

(51) Int. Cl.
*G06F 19/00* (2018.01)
*G06F 11/36* (2006.01)

(52) U.S. Cl.
CPC ......... *G16H 10/40* (2018.01); *G06F 11/3668* (2013.01); *G06F 19/324* (2013.01); *G16H 40/40* (2018.01); *G16H 70/00* (2018.01)

(58) Field of Classification Search
CPC .... G06F 19/324; G06F 19/34–19/3412; G06F 19/36–19/366; G06F 11/3668; G16H 10/40
See application file for complete search history.

(56) References Cited

U.S. PATENT DOCUMENTS

| | | | |
|---|---|---|---|
| 5,136,704 | A | 8/1992 | Danielsen et al. |
| 5,719,559 | A | 2/1998 | Talbott et al. |
| 5,980,081 | A | 11/1999 | Watari et al. |
| 6,173,440 | B1 | 1/2001 | Darty |
| 6,397,355 | B1 | 5/2002 | Curtis et al. |
| 6,640,203 | B2 | 10/2003 | Brown et al. |

(Continued)

FOREIGN PATENT DOCUMENTS

EP 0 997 819 A1 5/2000

OTHER PUBLICATIONS

Beizer, B., "Section 7.3 State Testing—Software Testing and Quality Assurance", 1984, pp. 79-87, Van Nostrand Reinhold, New York.

(Continued)

*Primary Examiner* — Michael Maskulinski
(74) *Attorney, Agent, or Firm* — K&L Gates LLP; Louis C. Cullman; Joseph Arand

(57) ABSTRACT

Disclosed is a clinical diagnostic analyzer employing a redundant error detection capability to further examine the internal message traffic for possible errors or questionable results by comparing the actual parameters against a fingerprint generated for each assay using an assay database and a configuration file. This testing does not rely on inputs from the software module being tested, and hence is an independent test. Further, a testing mechanism is provided to test the Redundant Error Detection ("RED") capability itself.

13 Claims, 7 Drawing Sheets

(56) References Cited

U.S. PATENT DOCUMENTS

| | | |
|---|---|---|
| 6,671,874 B1 | 12/2003 | Passova |
| 6,745,343 B1 | 6/2004 | Barenys et al. |
| 6,754,854 B2 | 6/2004 | Kurrasch |
| 6,757,714 B1 | 6/2004 | Hansen |
| 6,898,733 B2 | 5/2005 | Parks et al. |
| 7,254,601 B2 | 8/2007 | Bailer et al. |
| 7,302,677 B2 | 11/2007 | Reissman et al. |
| 7,366,678 B2 | 4/2008 | Greenstein et al. |
| 7,475,405 B2 * | 1/2009 | Manganaris .......... G06F 21/552 706/45 |
| 7,584,386 B2 | 9/2009 | Bancel et al. |
| 2002/0082886 A1 | 6/2002 | Manganaris et al. |
| 2002/0128801 A1 * | 9/2002 | Okuno ............. G01N 33/48792 702/187 |
| 2006/0136263 A1 | 6/2006 | Fry et al. |
| 2007/0217949 A1 * | 9/2007 | Mimura ........... G01N 35/00603 422/63 |
| 2007/0260932 A1 * | 11/2007 | Prichard ............. G06F 11/2215 714/39 |
| 2008/0312893 A1 * | 12/2008 | Denton ............ G01N 35/00613 703/11 |

OTHER PUBLICATIONS

EP Search Report for Application No. EP 09 25 1691 dated May 12, 2011.
EP Search Opinion for Application No. EP 09 251 691.3.
European Examination Report for EP 09 251 691.3; dated Mar. 1, 2017; 6 pages.
Canadian Office Action and Examination Search Report for CA 2,670,894; dated Dec. 7, 2016; 5 pages.
Canadian Office Action and Examination Search Report for CA 2,670,894; dated Nov. 27, 2017; 5 pages.
European Examination Report for EP 09 251 691.3; dated Dec. 12, 2017; 1 page.

* cited by examiner

REDUNDANT ERROR DETECTION IN A CLINICAL DIAGNOSTIC ANALYZER

CROSS-REFERENCE TO RELATED APPLICATIONS

This application is a continuation of co-pending U.S. application Ser. No. 12/493,689, filed Jun. 29, 2009, which claims priority from U.S. Provisional Application Ser. No. 61/077,245, filed Jul. 1, 2008, each of which is incorporated herein by reference in its entirety.

BACKGROUND

Repairing or correcting degraded assay performance in clinical analyzer systems has proven to be more difficult than correcting electrical or mechanical issues. Estimating the expected performance and monitoring the actual performance of clinical laboratory testing and diagnostic systems requires detailed and current information. Design and manufacturing clinical diagnostic systems requires testing and integration of thousands of components and subsystems in a complex software coordinated combination for carrying out accurate assays while maintaining a high throughput. An example is provided by the VITROS 4,3™ and ECi line of clinical Diagnostic Analyzers manufactured by Ortho Clinical Diagnostics ("OCD") of Raritan, N.J.

A clinical diagnostic analyzer contains extensive software monitoring and controlling its operation. Testing and examining every possible state of the analyzer is often not possible in view of the large number of states possible for the combination of software and hardware over the expected life and use of the analyzer. Testing the software in a clinical diagnostic analyzer is expensive, time consuming and difficult. For instance, if a subsystem in the analyzer fails, it is reduced, which is declared to be inactive, and needs to be restarted and initialized before use. Asynchronous messages, generated, for instance due to an unexpected opening of the cover of the incubation chamber, may require the affected replicates to be treated as potentially tampered with. Further, recovery from error conditions may affect multiple other tests due to exceeded limits, missed steps and many other undetected errors. Errors may also cause additional errors to ripple through multiple other tests. Further, such errors or their effect may not be detected in time by the routine process for controlling and regulating the operation of a clinical diagnostic analyzer because different tests may be affected to different degrees. The alternative often is to discard valuable patient samples in various stages of processing and restart the entire instrument, which results in reduced throughput and efficiency.

One of the goals in designing clinical diagnostic analyzers is to prevent the release of questionable laboratory results in view of the harm that may result to a patient from treatment or lack thereof based on erroneous results. Thus, timely error detection is of considerable importance in clinical diagnostic analyzers. Indeed, it is desirable to go beyond ensuring assay and equipment performance to merely satisfy health and safety guidelines in order to reduce the cost of assays while improving the reliability of assay results. At the same time, it is imperative to not discard valid results based on an over-inclusive criterion.

Laboratories use a wide range of techniques to help prevent incorrect or even potentially incorrect results from being released. These include but are not limited to assay control charts, equipment maintenance processes/logs, periodic analyzer maintenance, comparison to patient normal performance for the particular assay, reviewing changes since last result for a patient, grouping of results to calculate a physiologically stable quantity. All of these approaches are designed to react to a performance issue after results are released. Releasing a result typically means not only providing the result, but also indicating reliability of the result. Many checks are performed as infrequently as once a day and are suitable only for detecting long-term trends or frequent outliers or highly degraded performance. This puts the laboratory and patient at risk due to release of assay data with degraded performance for hours or even days before it is detected using these methods. In a busy lab, this can result in hundreds of patient samples being retested with a heightened risk of other than the desired treatment while laboratory throughput decreases.

Clinical diagnostic analyzers, like other complex systems comprising scheduler like controllers, control sub-systems using message traffic comprising commands, responses and asynchronous messages, interrupts and the like. Typically, the scheduler, usually implemented as a software module, controls the operation of the clinical diagnostic analyzer by allocating resources, scheduling the desired tests and tracking the performance of the various commands. The scheduler issues commands to various subsystems, which send back a response indicating the result of carrying out the command. The subsystems may, in turn, in response to receiving a command from the scheduler, send one or more commands to other software modules and receive messages from them indicating the result of executing the corresponding command.

All Subsystem Commands, Command Responses, and Asynchronous messages may be considered to be a subsystem input/output. The software module, a subsystem manager, writes these messages into Emulator Files. The Emulator Files, while voluminous, may be reviewed in course of trouble-shooting. This task, however, tends to be slow and impractical to flag and prevent questionable results from being released without inordinately delaying the release of results. Notably, clinical diagnostic analyzers typically support testing of STAT samples requiring expedited processing. Some additional strategies to track or estimate the performance of complex systems that are also not suitable for handling clinical diagnostic analyzers are describe next.

U.S. Pat. No. 7,254,601 (the "'601 patent") discloses a method for managing remotely deployed intelligent equipment, but, does not teach timely prevention of release of questionable laboratory results.

U.S. Pat. No. 6,757,714 (the "'714 patent") and patents and patent applications related thereto disclose obtaining and communicating an error condition of an apparatus via email to a remote server. A predefined template is used to generate the e-mail message by obtaining and inserting one or more variables into the template. The error condition may be included as part of a body of the e-mail message or as part of an attachment to the e-mail message. The error condition is reported using a self-describing computer language, such as eXtensible Markup Language (XML). In general, the error condition is determined with the aid of an embedded controller. The remote server passes the error condition to a customer relationship management system. The '714 patent does not address avoiding the release of erroneous results by preventing the machine from releasing questionable results due to unexpected scheduler or software errors.

What is needed is a reduction in the need to exhaustively review and test every possible state of a clinical diagnostic analyzer in order to ensure robust performance. Instead, better error detection strategies are needed to ensure reliability of results released by a laboratory.

SUMMARY

A preferred embodiment provides a system and method for detecting or predicting errors to prevent release of questionable laboratory test results. Briefly, the preferred embodiment employs a redundant error detection capability to further examine the message traffic for possible errors or questionable results by comparing the actual parameters against an expected fingerprint generated for each assay using an assay database and a configuration file or specification. This testing does not rely on inputs from the software module being tested, and hence is an independent test. For instance, if the scheduler software performs in unexpected ways, it is desirable to have an independent method to flag such errors before any results affected by such errors or issues are released. Further, a testing mechanism is provided to test the Redundant Error Detection ("RED") capability itself.

The fingerprint is generated, preferably dynamically, from (i) an assay database capable of providing protocol information for each assay, and (ii) hard-coded information in the form of a configuration file for the assay, replicate or device of interest. The fingerprint is a set of expected events required for successful completion of the test in question. At the same time, the number of events in a fingerprint typically is less than the exhaustive listing of events that are actually executed for the test. The reduction in the number of events in the protocol database to generate the fingerprint is guided by the configuration specification. Preferably, the configuration specification is merged with information from the assay database to generate the expected fingerprint.

With a generated fingerprint, RED reviews the message traffic and identifies discrepancies in the form of events required by the fingerprint that are absent from the message traffic to flag questionable results. RED can also review emulator files or data logging files to gain access to the message data and identify discrepancies after results have been processed. This ability is useful in validating and testing software including validating newer versions of RED itself in an economical manner.

In another aspect, RED is integrated into existing analyzers easily because it requires few modifications and leaves the subsystem input-output traffic largely unchanged.

A preferred embodiment comprises a module executable on a processor in a clinical diagnostic analyzer for detecting questionable laboratory results in the clinical diagnostic analyzer. The module includes a mechanism for receiving a copy of messages comprising Subsystem Commands, Command Responses, and Asynchronous messages. The module also includes a fingerprint of expected events to be tested for a replicate. The fingerprint is generated, in response to a preview replicate command, from at least a configuration file and an assay database, wherein the assay database contains details for an assay required by the replicate. The module includes instructions for completing a comparison, in response to a replicate check command, between the received messages and the fingerprint. The module includes instructions for reporting a result of the comparison; and releases resources required for the redundant checking of the replicate, in response to receiving a replicate complete command.

In the preferred embodiment, the RED functionality may be readily turned off by an operator dynamically. This may be useful if an error in RED is suspected. If a failure or questionable results are detected, the RED functionality logs corresponding conditions. Such logging notifies the operator of the detected condition and is useful in debugging and improving software. However, the decision to not release results may be turned off until suspected problems in RED itself are resolved.

This disclosure includes a method for testing a software module in a clinical diagnostic analyzer. The method comprises the steps of generating subsystem commands, command responses, and asynchronous messages suitable for delivery to a redundant error detector. The redundant error detector reviews the generated subsystem commands, command responses, and asynchronous messages for inconsistencies. In the event such inconsistencies are identified, the software module is debugged to ensure reliable and consistent performance. Notably, the software module being tested could be the redundant error detector software. Further, part of or an entire system comprising software modules may be tested in this manner.

The subsystem commands, command responses, and asynchronous messages are advantageously generated from a script file containing a record of one or more prior runs of the analyzer. Then the performance of the clinical diagnostic analyzer with alternative versions of the software can be compared using the redundant error detector to detect inconsistencies in any of the required events in a fingerprint. The script file can include commands in addition to data from the example operation of the clinical diagnostic analyzer.

In another aspect, a preferred embodiment is a method for preventing release of a questionable result by a clinical diagnostic analyzer. The method comprises facilitating the steps of receiving a preview replicate command for a replicate; allocating resources for redundant error checking for the replicate; generating a fingerprint of required events for the replicate using at least a configuration file and an assay database, wherein the fingerprint has fewer events than the events that could be generated from the assay database for the replicate; comparing messages corresponding to processing out the replicate with the fingerprint; sending a result of the comparison to prevent the release of a result corresponding to the replicate by the clinical diagnostic analyzer; and logging conditions corresponding to the replicate. It should be noted that allocation and release of resources required for redundant error checking need not be express and instead may be handled by the operating system or other functionality automatically depending on the system or the underlying programming language. Advantageously, the configuration file is coded in eXtensible Markup Language for implementation flexibility, which makes it readable by humans and easy to send as text to remote analyzers.

These and other features in some preferred embodiments are described below in greater detail with the aid of illustrative figures. These and other features in some preferred embodiments are described below in greater detail with the aid of illustrative figures and modules or submodules. In a preferred embodiment, a module (and a sub-module) reflects functional partitioning. A module or sub-module may use shared resources to perform its function. Resources typically are processor time slices, database data, data in memory shared with other modules, sub modules, shared library functions and the like as is well known to one having ordinary skill in the art. A developer, having ordinary skill in the art, knows how to create a module. Mapping the functional partitioning into executable code is familiar to one having ordinary skill in the art. The figures are briefly described next.

DETAILED DESCRIPTION OF THE PREFERRED EMBODIMENTS

Figure 1:
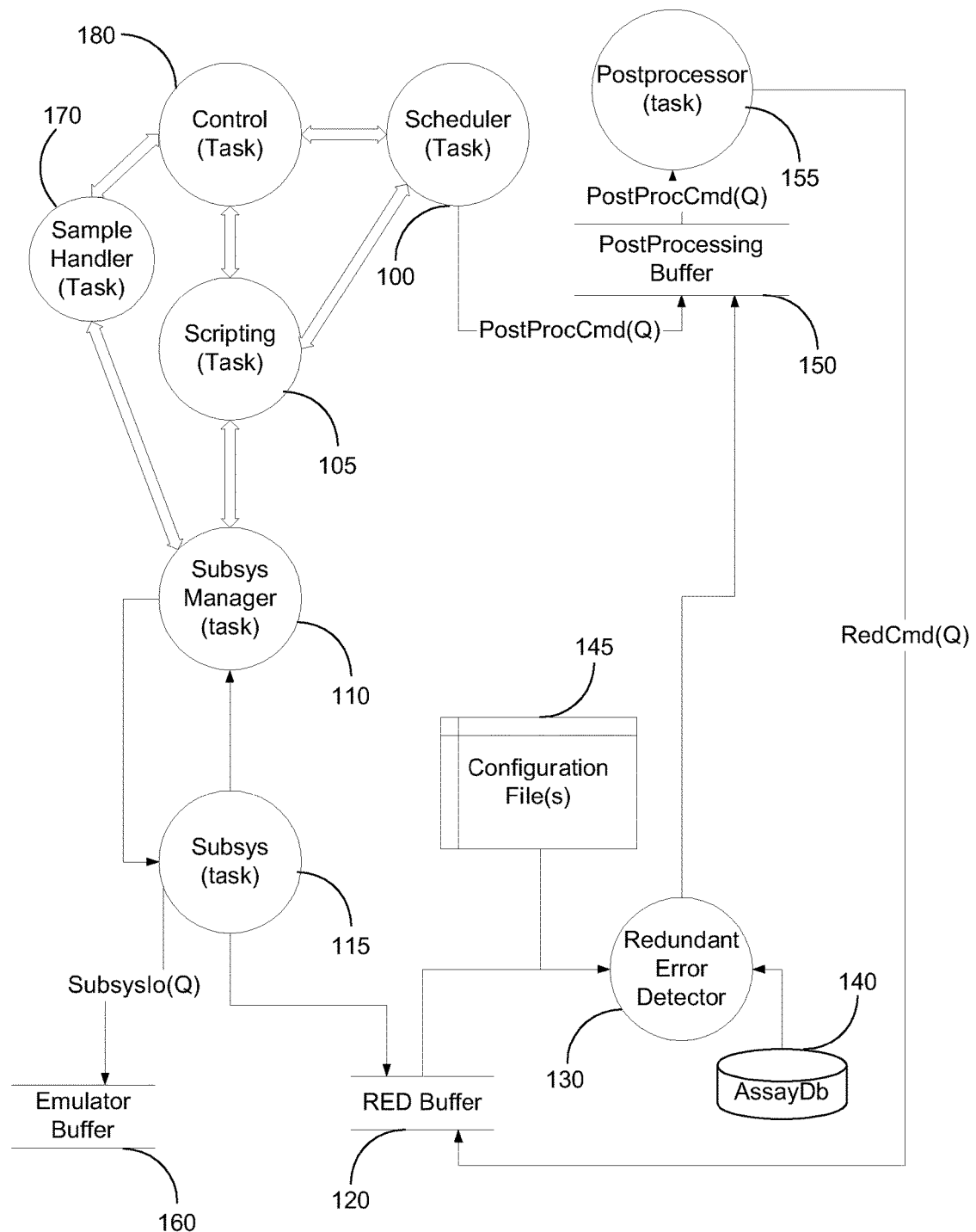
FIG. 1 illustrates a schematic of the processing modules in a clinical diagnostic analyzer coupled to a redundant error detector.

A 'basic event' in a clinical diagnostic analyzer, typically, is the detection of one or more parameters or a change therein. The parameters are values or descriptors of a state of the clinical diagnostic analyzer. An event occurs upon fulfillment of one or more specified conditions. A large number of such basic events are typically predefined for clinical diagnostic analyzers. The message traffic comprising commands, responses and asynchronous messages is an example of a subset of events of interest.

Redundant Error Detector ("RED") module, a software feature, detects discrepancies between sequences of expected events and actually observed events in the course of operating an analyzer or another sophisticated processing system. Sequences of expected events are formulated to provide a fingerprint for each test type run to avoid repeated exhaustive review of all events. RED provides not only software verification but also regression testing of replicate runs. In this context, an event denotes detection of one or more parameters or a change therein. Some examples of events include issuing of or receiving a command, making a measurement, issuing or receiving a response to confirm execution of a command, an interrupt and the like.

RED is compatible with OCD's clinical diagnostic analyzer VITROS 5600® and VITROS 3600®, which provide a preferred platform for implementing RED. RED is expected to be useful to other clinical diagnostic analyzers as well. Each of VITROS 5600® and VITROS 3600® use functions provided by a Master Scheduler, which can support multiple and different types of chemistry platforms. OCD's Master Scheduler can also control a robotic arm and pipettors shared between the various platforms to provide random access to input patient samples, which improves throughput. The random access to the input samples substantially eliminates the typical requirement to process samples in the order they are input.

OCD's Master Scheduler performs scheduling functions, for instance, to allocate resources to samples input in any order. Other not so versatile schedulers also benefit from the addition of the RED functionality. OCD's Master Scheduler determines a schedule to minimize the Time to Complete for the tests as a whole thereby maintaining high throughput while honoring applicable protocol restrictions.

The benefits of OCD's Master Scheduler include the synergistic effects of two-dimensional random access to the input samples while providing access to resources including, for example, multiple platforms, supply of consumables including thin film slides, reaction vessels and cuvettes, along with a plurality of sensitometric devices such as electrometers, reflectometers, luminescence, light transmissivity, photon detection, an incubator for heating the samples, a supply of reagents, and a plurality of reagent delivery subsystems, all of which can be accessed and used readily.

This functionality naturally entails additional complexity, which, in turn, requires testing to ensure reliability. RED provides additional assurances against the release of questionable results. Typically, a manufacturer of a clinical diagnostic analyzer provides a master list of details of supported assay protocols with its analyzers. This master list of protocol details may be edited to various degrees to add or modify the supported tests. The protocol details are stored in an assay database, or acquired from another information source, which is consulted for each supported assay by a preprocessing module to generate the parameters and resources required by a test. Although protocol details may not be in the form of events expected on the corresponding analyzer, such events can be generated using knowledge of a particular analyzer. The Scheduler uses the protocol details to allocate resources and schedule various steps to improve throughput and ensure quality.

To run each test, the Scheduler module issues multiple commands to the subsystem modules. When a command is carried out, various measurements are made, gears may turn or other operations take place and a response message is sent back to the scheduler to confirm the command was carried out successfully to complete the loop. If a subsystem detected unsuccessful execution of the command, then the corresponding response sent to the Scheduler typically includes this information.

Nevertheless, undetected errors in the operation of clinical analyzers are an expensive and undesirable reality. For instance, if a sub-system fails, it is 'reduced,' that is made unavailable and all replicates requiring the use of the reduced sub-system stall. However, other tests continue to progress to best use the analyzer resources. To ensure reliability, the reduced sub-system is restarted prior to processing samples, which procedure makes the sub-system performance predictable, but may cause unanticipated delays and perturbations in the scheduling. Similar uncertainty may result due to unplanned events, such as an operator opening the cover of an incubation chamber and potentially contaminating all samples contained therein. Scheduler software may have anomalies resulting in a particular step not being followed. If the failure to perform the step is a rare occurrence, it may not be detected readily during testing. Some such errors in the Scheduler software may be exacerbated by unplanned events such as reduction of various sub-systems, initialization of these sub-systems, and other interruptions.

A preferred embodiment provides a system and method for detecting or predicting errors to prevent release of questionable laboratory test results. A list of required events, as opposed to all possible events, for each supported test is prepared in advance in the form of a configuration file. This configuration specification is preferably defined in an eXtensible Markup Language ("XML") format.

There are many advantages in using XML. XML is useful for defining events, including those that are combinations or variations of basic events. XML encoded instructions and descriptions can be implemented and debugged rapidly in real time using an interpreter. Further, XML based definitions are readily communicated by treating them as text. However, XML tags, although readable by humans, often describe very different functions and data using similar or even the same tag names. Nevertheless, in a context XML provides a description of the functions performed by executing XML compliant instructions. Therefore, given a proper context, XML provides a convenient method for communicating data, instructions and combinations thereof.

In effect, a specific instance of XML designed to facilitate a particular set of tasks at a target creates a "new machine" capable of performing particular functions. Thus, a circuit performing function(s) specified by one or more XML tags in response to interpreting XML encoded instructions is a structure performing the indicated function(s).

An example event described using XML in a configuration specification is shown below:

```
<?xml version="1.0" ?>
- <!-- $Id: RED_MsPmRepSeq.xml,v 1.8 2008/03/31 14:04:05 mreed7 Exp $
-->
- <RED_STEP RED_STEP_NAME="RED_MsPmRepSeq"
RED_STEP_DESC="MicroSlide PM Replicate">
    - <RED_EVENT RED_EVENT_NAME="Aspirate ERF command"
RED_EVENT_DESC="Aspirate ERF command">
        - <RED_CRITERIA_SET>
        <RED_CRITERIA RED_EVENT_TOKEN_NAME="EVENT_TYPE"
RED_CRITERIA_VALUE="CMD" />
        <RED_CRITERIA RED_EVENT_TOKEN_NAME="DEV"
RED_CRITERIA_VALUE="DRY_REF_MET_PUMP_DEV"/>
        <RED_CRITERIA RED_EVENT_TOKEN_NAME="CMD"
RED_CRITERIA_VALUE="ASPIRATE" />
        </RED_CRITERIA_SET>
        - <RED_ACTION
RED_ACTION_NAME="RED_SET_SEQ_START_TIME_IF_NOT_SET"
RED_ACTION_COMMENT="Set the start time of the sequence to equal the event time
plus the offset" RED_EVENT_TOKEN_NAME="TIME"
RED_ERROR_ID="1">
            - <RED_LIST RED_LIST_TYPE_NAME="PRIM"
SC_SCRIPT_DATA_NAME="RED_EVENT_MS_TIME_INTERNAL">
            <RED_VALUE RED_VALUE_TYPE_NAME="RED_STATIC_VALUE"
RED_VALUE_VALUE="-1800" />
            </RED_LIST>
        </RED_ACTION>
        - <RED_ACTION
RED_ACTION_NAME="RED_CHECK_EVENT_EQ_CFG_TIME_RANGE"
RED_ACTION_COMMENT="Check that the event starts within the specified time
range from the start of the step." RED_EVENT_TOKEN_NAME="TIME"
RED_ERROR_ID="2">
            - <RED_LIST RED_LIST_TYPE_NAME="PRIM"
SC_SCRIPT_DATA_NAME="RED_EVENT_MS_TIME_INTERNAL">
            <RED_VALUE
RED_VALUE_TYPE_NAME="RED_PREVIEW_MSEC_TIME_RANGE_VALUE"
RED_VALUE_VALUE="0" />
            <RED_VALUE
RED_VALUE_TYPE_NAME="RED_PREVIEW_MSEC_TIME_RANGE_VALUE"
RED_VALUE_VALUE="6550" />
            </RED_LIST>
        </RED_ACTION>
        - <RED_ACTION
RED_ACTION_NAME="RED_CHECK_DEV_EQ_CFG_PARAM"
RED_ACTION_COMMENT="RefMet CAM positioned for aspirate"
RED_DEVICE_NAME="RED_MS_REF_MET_DEV" RED_ERROR_ID="7">
            - <RED_LIST RED_LIST_TYPE_NAME="PRIM"
SC_SCRIPT_DATA_NAME="REF_MET_CAM_POS">
            <RED_VALUE RED_VALUE_TYPE_NAME="RED_STATIC_VALUE"
RED_VALUE_VALUE="RESERVOIR" />
            </RED_LIST>
            - <RED_FAIL_CMDS>
            <RED_TEST_CMD RED_TEST_CMD_NUMBER="69" />
            </RED_FAIL_CMDS>
        </RED_ACTION>
        - <RED_ACTION
RED_ACTION_NAME="RED_CHECK_EVENT_EQ_DEV_PARAM_BY_TIME_RA
NGE" RED_ACTION_COMMENT="Check that RefMet has been used in last 15
Minutes" RED_DEVICE_NAME="RED_MS_REF_MET_DEV"
RED_ERROR_ID="8">
            - <RED_LIST RED_LIST_TYPE_NAME="PRIM"
SC_SCRIPT_DATA_NAME="TIME_INTERNAL">
            <RED_VALUE RED_VALUE_TYPE_NAME="RED_STATIC_VALUE"
RED_VALUE_VALUE="{ 0 0 }" />
            <RED_VALUE RED_VALUE_TYPE_NAME="RED_STATIC_VALUE"
RED_VALUE_VALUE="{ 900 0 }" />
            </RED_LIST>
        </RED_ACTION>
    </RED_EVENT>
</RED_STEP>
```

In the above event specification, one event is described within a "RED STEP" tag, although multiple events are typically describe in configuration specifications, which may be in the form of configuration files. A set of criteria describing tags provide background and contextual information followed by multiple "RED ACTION" tag sets, within each of which may be nested "RED LIST" tags, within each of which may be listed "RED VALUE" tags describing individual requirements defining conditions for satisfying the event. All events so defined must be satisfied in the preferred embodiment by the message stream corresponding to a test of interest for the results of the test to be validated. Further, parameters to be passed in the event of failure or success may also be included along with comments and other commands or instructions. As will be apparent, this is not the only scheme for specifying events in a fingerprint. Alternative tag sets may be devised with no loss of generality or the interpretation of particular tags modified without departing from the sprit of the disclosed preferred embodiment.

Accordingly, at runtime a more complete description of required events, a fingerprint, for each test is generated using the assay database in combination with the configuration specification. This approach not only conserves required memory resources, but also provides flexibility because updates or changes to the assay database or the configuration specification are automatically reflected in the generated fingerprint.

As shown in FIG. 1, Scheduler 100 communicates with various subsystems including Scripting 105, which in turn, has a two-way communications with the Subsystem Manager 110. Subsystem Manager 110 issues a command to Subsystem 115 and receives a response confirming execution of the command as is shown. The Subsystem Manager 110 typically sends the message traffic comprising commands and responses as well as asynchronous messages to an Emulator File 160 and to RED Buffer 120, which is a mechanism for transferring messages and information to Redundant Error Detector 130. A preferred RED Buffer 120 is implemented as a queue.

Scheduler 100 also sends commands to Postprocessor 155 by sending commands to a Postprocessing Buffer 150. Postprocessor 155 sends commands to a RED Buffer 120. RED Buffer 120 also receives a copy of the message traffic being recorded in Emulator File 160. Thus, Redundant Error Detector 130 receives as input the message traffic comprising commands and responses as well as asynchronous messages and commands from Postprocessor 155. Further, Redundant Error Detector 130 has access to Configuration File 145.

Control 180 controls Scheduler 100 through a two-way linkage. Similar linkages connect Sample Handler 170 to Control 180 and the Subsystem Manager 110. Under the direction of Control 180, required test instructions for an input set of patient samples are converted by a preprocessor functionality, using Assay Database 140, to commands for Scheduler 100. Scheduler 100 then allocates resources and issues commands to carryout the instructions. As noted, the expected execution order of events by Scheduler 100 may not always hold true.

Figure 3:
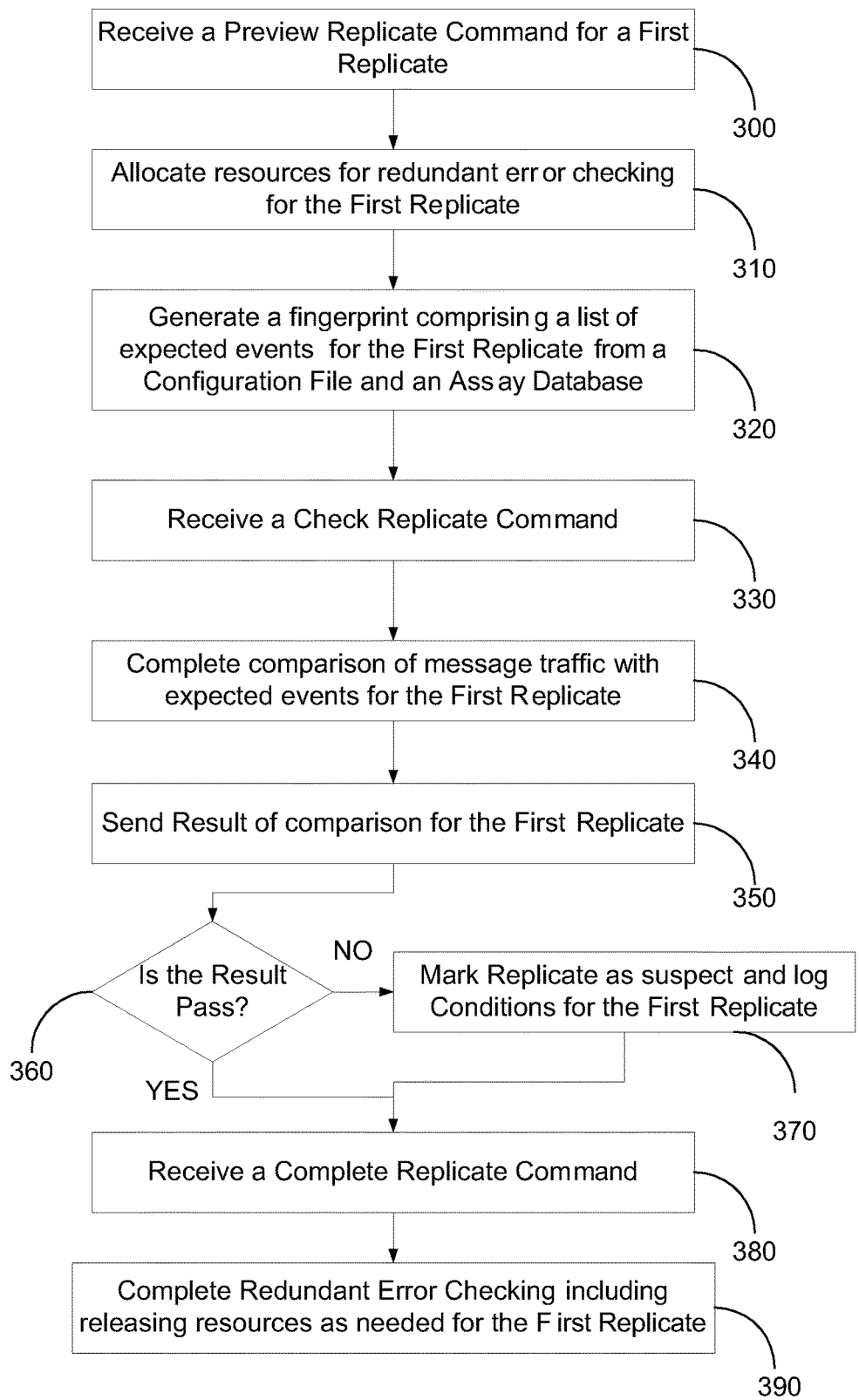
FIG. 3 illustrates the redundant error detection functionality and various components within it or closely interacting with it, which may further integrated.

FIG. 3 illustrates the role of Redundant Error Detector 130 in providing an independent test on the results to identify questionable results without increasing the complexity of Scheduler 100 or other components. At the start of a replicate, during step 300, Postprocessor 155 sends a Preview Replicate command to RED Buffer 120. In response to this command, Redundant Error Detector 130 allocates resources during step 310 and generates a fingerprint by using Configuration File 145 and Assay Database 140 to determine the parameters and nature of events to be checked for in the message traffic, also received at RED Buffer 120.

The fingerprint is generated, preferably dynamically, from (i) an assay database capable of providing protocol information for each assay or replicate, and (ii) hard-coded information in the form of a configuration file for the assay, replicate or device of interest. The fingerprint is a set of expected events required for successful completion of the test in question. At the same time, the number of events in a fingerprint typically is less than the exhaustive listing of events required to execute the test. Configuration File 145 defines a list of expected events for a given step in a protocol. The reduction in events reduces the effort required of RED as well as the complexity of RED.

A preferred fingerprint includes critical events, whose performance is necessary to generate a reliable result and events that improve the accuracy of the results. Critical events' successful completion may itself indicate successful completion of many events that are not expressly checked as part of the fingerprint.

In the preferred embodiment, parameters configurable per assay are read from the Assay Database 140 at run-time. In this preferred embodiment, the expected events of MicroSlide and SI replicates (run on two types of platforms) are completely defined by a single configuration file in Configuration File 145 while the expected events corresponding to a MicroWell and MicroTip replicate (run on two additional types of platforms) are defined by merging multiple configuration files together. In this preferred embodiment, each configuration file defines one protocol step and Assay Database 140 is queried to determine the protocol steps required to run each replicate. At runtime Redundant Error Detector 130 generates the list of expected events by merging Configuration Files 145 corresponding to each protocol step of the given assay type. Each command event within a replicate step contains an action that causes Redundant Error Detector 130 to check that the event occurred within an allowed time range. At runtime (as the steps are merged together) the allowed time ranges are modified based upon step durations and incubation durations.

Redundant Error Detector 130 preferably processes each event for all devices prior to processing the event for all pending replicates. Each event received by RED is compared to each expected event within each Device Sequence in the order in which the expected events are defined. If an event matches one set of criteria defined for that expected event then the actions defined within that expected event are executed. Once a received event matches one expected event within a Device Sequence (which is the definition of the events, criteria, actions, and parameters that correspond to one device) no other expected events within that Device Sequence will be checked or executed until the next event is received from RED Buffer 120.

Figure 6:
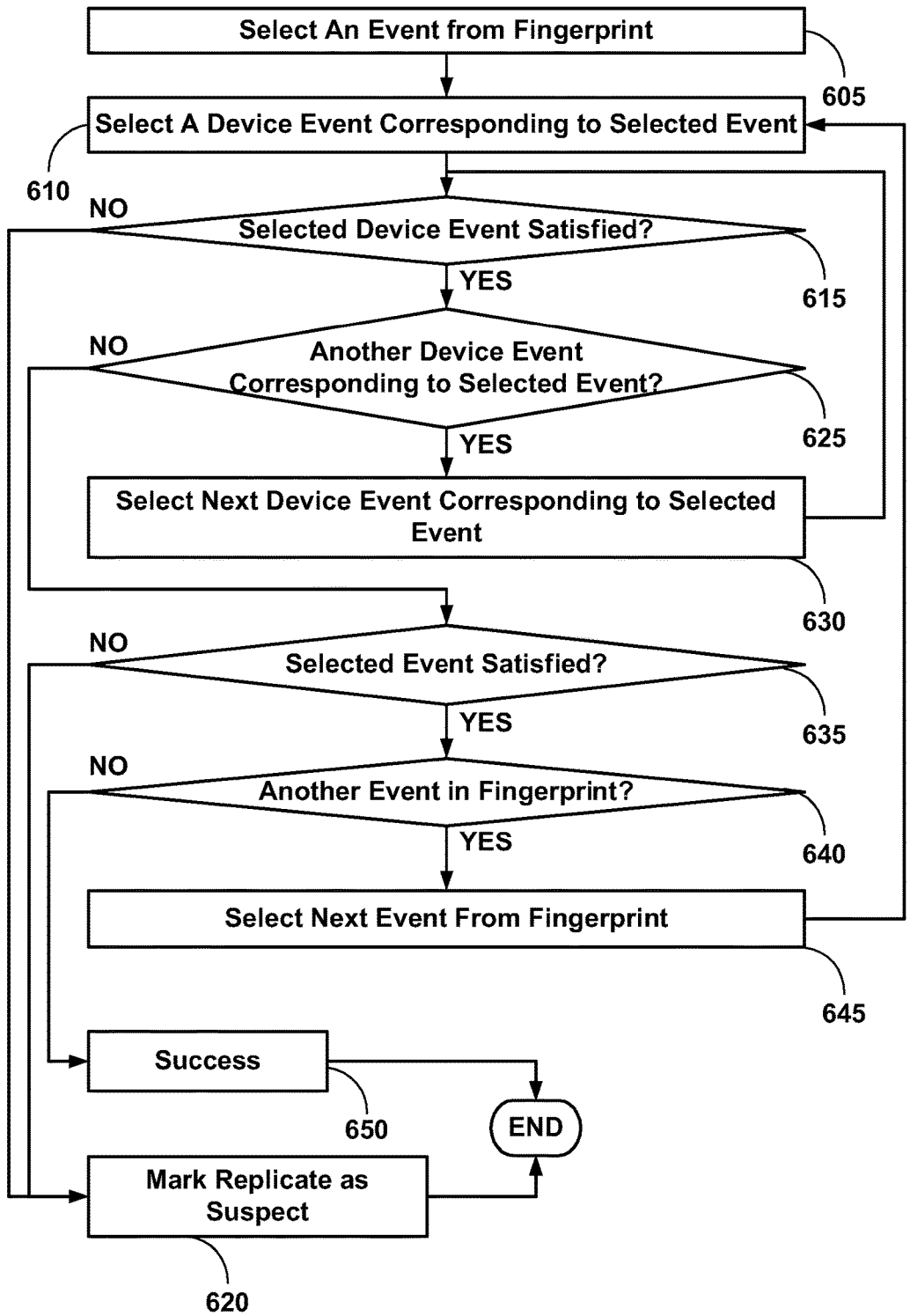
FIG. 6 illustrates the redundant error detection functionality and various components within it or closely interacting with it, which may be further integrated.

FIG. 6 further describes one such exemplary preferred method for testing using RED. During step 605 an event is selected from a generated fingerprint. This is followed by the selection of a Device Event corresponding to a selected fingerprint event during step 610. Device Events are preferably specified in the configuration specification. They, however, are not merged with the assay protocol information as is the case with generating a fingerprint. Instead, they are used to independently evaluate device state. A Device Event verifies the state of a device at the time an event of interest takes place.

For instance, if a reading is obtained from an optical reader in a selected event, then a corresponding device event may be to check if the optical reader was tested against a control within a prescribed period of time prior to the test reading, and possibly an event after the test reading was taken to ensure the optical reader was fully functional. Failure in one or both of these device events, checked by comparing to the device state immediately preceding and following the test reading may mark a replicate as suspect. Thus, failure in a Device Event, checked by comparing to the device state immediately preceding and following the test reading, may identify a suspect replicate.

Control flows from step 610 to decision step 615 during which the selected device event is tested in view of a message in the message stream being monitored to ensure it is satisfied. If the event is not satisfied then control flows to step 620 to mark the replicate as suspect and the method concludes. Other embodiments may allow the method to continue to execute with no loss of generality. Alternatively, if the event is satisfied, control flows to step 625 during which the need to evaluate another device event is evaluated. If there is at least one additional device event at this stage, control flows to step 630 to select another device event and control returns to step 610.

Alternatively, if there are no further device events corresponding to the fingerprint event selected in step 605, the selected event is evaluated in step 635. If the selected event is satisfied, then, control flows to step 640 to determine if there are additional events in the fingerprint. Another event is selected, then, during step 645, if possible, and control returns to step 610. Else, control flows to step 650 to mark successful matching of the fingerprint with the message stream or event data being examined. The method then concludes. As is readily appreciated, this method is suitable for analyzing a message stream—including message streams not analyzed in real-time or those that are generated by a simulation.

Expected events may differ between platforms and analyzers. Preferred implementation of Redundant Error Detector 130 primarily evaluates two types of events: (i) Replicate Events; and (ii) Device Events. This is illustrated in the preferred exemplary embodiment illustrated in FIG. 7.

During step 700 a message in received as part of the monitored message traffic. During step 705, the message is used to update a description of Device State information, if applicable, maintained by RED. In a preferred embodiment, RED maintains state for each device of interest, which states are based on the message traffic monitored by RED. It should be noted that not all messages resulting in updating of device state may be part of the relevant fingerprint.

The received message is next employed to test for device events. A Device Event is selected during step 710. Device Events are preferably specified in the configuration specification. They, however, are not merged with the assay protocol information as is the case with generating a fingerprint. Instead, they are used to independently evaluate device state. A Device Event verifies the state of a device at the time an event of interest takes place. Failure in a Device Event, checked by comparing to the device state immediately preceding and following the test reading, may identify a suspect replicate.

Control flows from step 710 to decision step 715 during which the selected device event is tested in view of the message to ensure it is satisfied. If the event is not satisfied then control flows to step 720 to mark the replicate as suspect. Alternatively, if the event is satisfied, control flows to step 725 during which the need to evaluate another device event is evaluated. If there is at least one additional device event at this stage, control flows to step 730 to select another device event and control returns to step 715.

Alternatively, if there are no further device events, an event is selected from the corresponding fingerprint during step 735. The selected event is evaluated in step 740 in view of the message. If the selected event is satisfied, then, control flows to step 745 to determine if there are additional events in the fingerprint. Another event is selected, then, during step 750, if possible, and control returns to step 740. Else, control flows to step 755 to mark successful matching of the fingerprint with the message stream or event data being examined. The method then concludes. As is readily appreciated, this method is suitable for analyzing a message stream—including message streams not analyzed in real-time or those that are generated by a simulation.

Replicate Events

Some examples of Replicate Events in a preferred embodiment are:

MicroSlide PM Replicate is a set of critical events required to process a Potentimetric MicroSlide replicate An example MicroSlide PM Replicate preferably includes multiple events such as:

Event #1: Aspirate command;
Event #2: Aspirate response;
Event #3: Plunge Slide Supply Cart command;
Event #4: Plunge Slide Supply Cart response;
Event #5: Dispense slide from cart command;
Event #6: Dispense slide from cart response;
Event #7: Dispense sample to slide command;
Event #8: Dispense sample to slide response;
Event #9: Dispense to slide command;
Event #10: Dispense to slide response;
Event #11: Push slide to Ring command;
Event #12: Push slide to Ring response;
Event #13: Electrometer Read command; and
Event #14: Electrometer Read response.

Each event requires some conditions to be met as described by specified parameters. For instance, Event #11, Push slide to PM Ring command, requires testing that the event starts within the specified time range from the start of the step. Other events, such as Event #10 require just 'success' to be tested to pass. Additional non-exhaustive examples of Replicate Events include MicroSlide CM Replicate Incubating in the Outer Ring is a set of critical events critical events required to process a Colormetric or Rate MicroSlide replicate that performs is major incubation period within the outer ring of the CM Rate Incubator.

MicroSlide CM Replicate Incubating in the Inner Ring is a set of critical events required to process a Colormetric or Rate MicroSlide replicate that performs is major incubation period within the inner ring of the CM Rate Incubator.

MicroSlide IR Replicate is a set of critical events required to process a ImmunoRate MicroSlide replicate.

MicroTip Reagent Addition Step is a set of critical events required to process the step where reagent is added to a cuvette within a MicroTip replicate.

MicroTip Sample Addition Step is a set of critical events required to process the step where neat sample is added to a cuvette within a MicroTip replicate.

MicroTip Diluted Sample Addition Step is a set of critical events required to process the step where diluted sample is added to a cuvette within a MicroTip replicate.

MicroTip Read Step is a set of critical events required to process the step where the cuvette is read using the Photometer within a MicroTip replicate.

MicroWell 1st Well Pretreatment Step is a set of critical events required to process the step where neat sample is added to a pretreatment well within a MicroWell replicate.

MicroWell Not 1st Well Pretreatment Step is a set of critical events required to process the step where diluted sample is added to a pretreatment well within a MicroWell replicate.

MicroWell 1st Well Dilution Step is a set of critical events required to process the step where neat sample is added to a dilution well within a MicroWell replicate.

MicroWell Not 1st Well Pretreatment Step is a set of critical events required to process the step where diluted sample is added to a dilution well within a MicroWell replicate.

MicroWell Reagent Addition Step To Middle Ring Well is a set of critical events required to process the step where reagent is added to a pretreatment well or a dilution well within a MicroWell replicate.

MicroWell Reagent Addition Step To Outer Ring Well is a set of critical events required to process the step where reaction well within a MicroWell replicate.

MicroWell 1st Well Sample Step is a set of critical events required to process the step where neat sample is added to a reaction well within a MicroWell replicate.

MicroWell Not 1st Well Sample Step is a set of critical events required to process the step where diluted or pretreated sample is added to a reaction well within a MicroWell replicate.

MicroWell Preliminary Wash Step is a set of critical events required to process the step where a reaction well receives its preliminary well wash within a MicroWell replicate.

MicroWell Final Wash Step is a set of critical events required to process the step where a reaction well receives its final well wash and is read using the Luminometer within a MicroWell replicate.

Sample Integrity Step is a set of critical events required to process Sample Integrity readings of a sample.

Device Events

Some preferred examples of device events include those for MicroSlide Electrometer. Independent of the sample slide, the electrometer reads a reference slide to ensure at least one successful read of a reference slide within a prescribed time period. Specifying multiple critical events included in a fingerprint captures this requirement. Other devices with critical events specified may include incubation rings or areas, conveyor or ring transport mechanisms, shuttles, metering devices, controls on metering, reflectometers, slide supplies, buffer rings, movement arms, STAT lanes, reagent supplies, washing stations, blade insertors, blade dumpers, photometers and the like. This list is not exhaustive.

Figure 7:
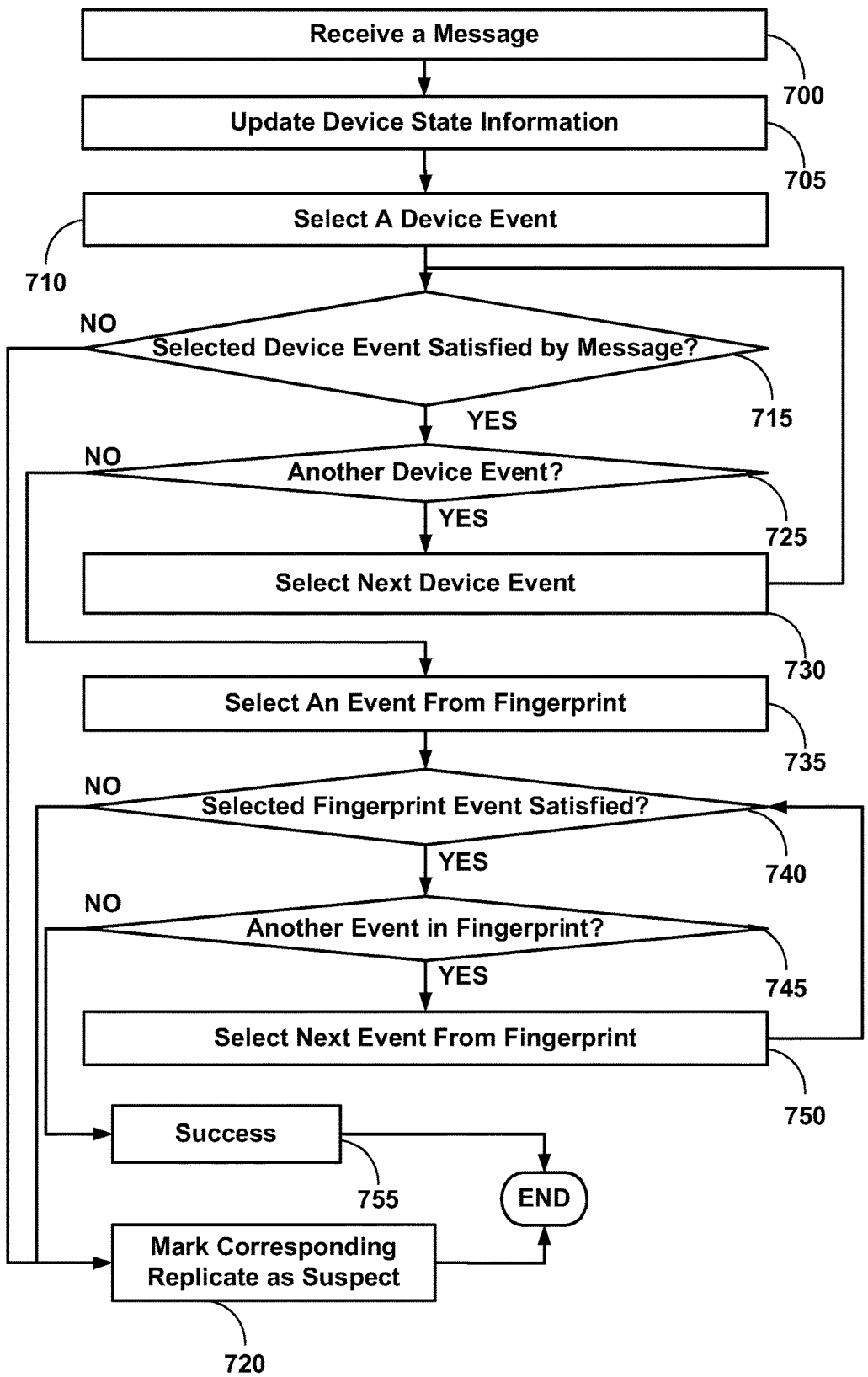
FIG. 7 illustrates an example redundant error detection functionality checking a message stream for device and replicate events while updating device state maintained by the redundant error detection functionality.

With a generated fingerprint, Redundant Error Detector 130 reviews the message traffic and identifies discrepancies in the form of events required by the fingerprint that are absent from the message traffic. For each received message, RED preferably matches Replicate and Device Events in a fingerprint as illustrated in FIG. 7 to perform associated actions.

In step 340 of FIG. 3, in response to receiving a Check Replicate command in step 330, Redundant Error Detector 130 completes the discrepancy identification survey by reviewing messages with a time stamp between that of the Preview Replicate command and the Check Replicate command. Results corresponding to such discrepant events are flagged as questionable.

During step 350, Redundant Error Detector 130 sends the result of identifying discrepancies to Postprocessing Buffer 150, which is a mechanism for transferring messages and information to Postprocessor 155. If the result is determined to be questionable in step 360, then, Redundant Error Detector 130 also identifies the test result as suspect with logging of the corresponding conditions during step 370. Finally, during step 380 a Complete Replicate command is received. Questionable results are preferably not released by Postprocessor 155, and naturally by the clinical diagnostic analyzer. If needed, sequestered resources are released during step 390.

Figure 2:
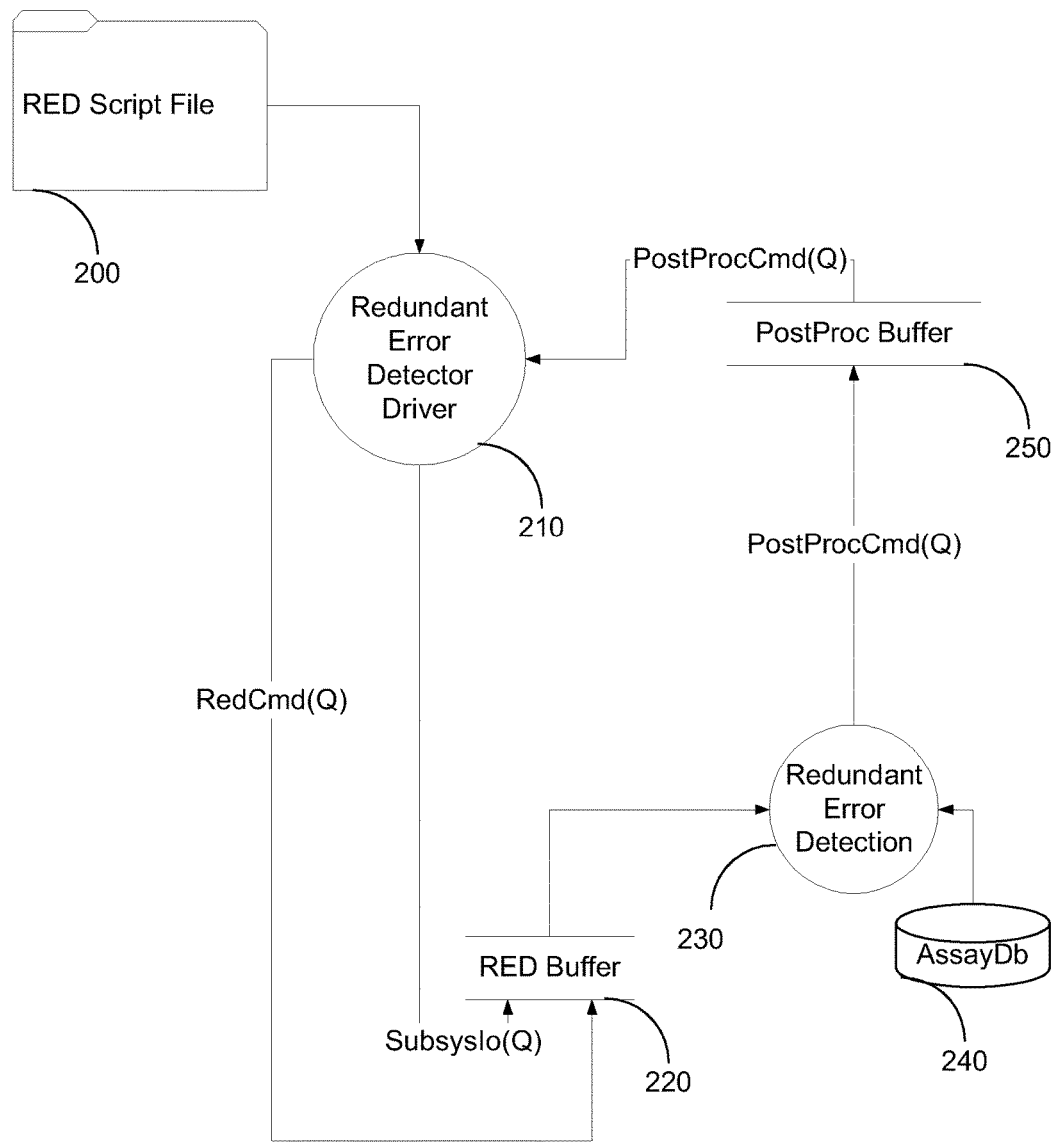
FIG. 2 illustrates a schematic of a software testing arrangement using a redundant error detector.

Redundant Error Detector can also review emulator files or data logging files to gain access to the message data and identify discrepancies in a non-real-time mode. This ability is useful in validating and testing software including validating newer versions of RED itself in an economical manner. FIG. 2 shows a preferred configuration for such testing while FIG. 4 illustrates some of the steps in the preferred embodiment.

Figure 4:
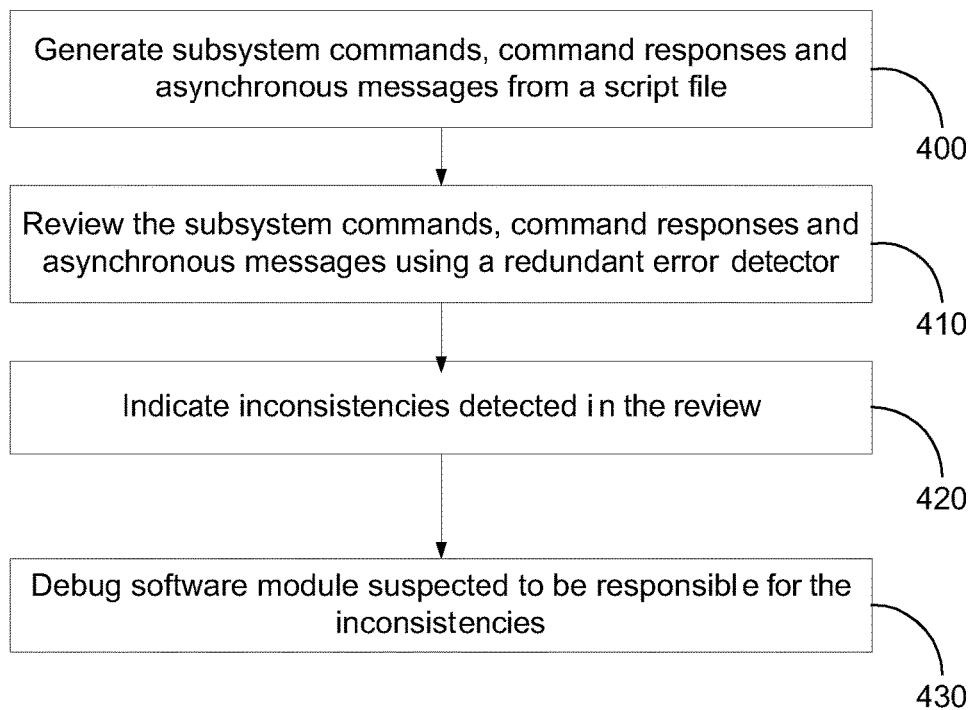
FIG. 4 illustrates a method for checking for errors using a redundant error detector.

During step 400 of FIG. 4, a script file, RED Script File 200 is used by Redundant Error Detector Driver 210 to generate ordered entries for RED Buffer 220. RED Script File 200 is a record of messages in an example operation of the clinical diagnostic analyzer coupled with some commands typically to assist in the testing. Redundant Error Detector 230 processes RED Buffer 220 to match a dynamically generated fingerprint using configuration files and Assay Database 240. The result of the processing by Redundant Error Detector 230 is sent to PostProc Buffer 250, which in turn leads back to Redundant Error Detector Driver 210, which evaluates the performance of the test software—and may lead to debugging the same. The test software preferably is Redundant Error Detector 230. Alternatively, the test software may be a module used in the example operation to generate data reflected in RED Script File 200. The data reflected in RED Script File 200 in alternative embodiments is from an emulator file generated as depicted in FIG. 1 or even a datalogger file being mined to identify errors in an analyzer under investigation. Redundant Error Detector Driver 210 is responsible for converting all these potentially different formats to one suitable for action by Redundant Error Detector 230.

In another aspect, RED is integrated into existing analyzers easily because it requires few modifications and leaves the subsystem input-output traffic largely unchanged. This is readily seen from FIGS. 1 and 2, wherein Redundant Error Detector 230 is connected without significantly affecting the inner message traffic of the clinical diagnostic analyzer. Preferably, RED can be configure dynamically, for instance, to release all results. Thus, preferably it is possible to control or configure the penalty imposed by RED when an anomaly is detected.

Goals for an efficient error detection system include timely detecting errors to prevent release of erroneous results. The configuration files define the checks performed by RED. Thus, for each assay model type RED preferably checks for events critical to result quality; events detrimental to result quality; Pass/Fail/Warn criteria, if any, for each event; and required sample consistency checks.

In most instances, the events checked for by RED are also checked for by the routine command-response design of the clinical diagnostic analyzer or other system of interest. In view of the small impact of RED on analyzer performance, implementing RED does not significantly delay the release of acceptable results.

In an effort to reduce the likelihood of RED preventing the prediction of good results helpful guidelines include limiting the number of events checked to only the required events; correctly setting the valid ranges of parameters to account for all scenarios; and providing configurability to prevent the RED module from being able to fail results even when it is suspected to be malfunctioning.

Further, the RED module itself is tested to verify all checks are executing correctly in the foreseen scenarios. This may be performed by, for instance, the simulation strategy presented in FIG. 2.

Alternative Error Detection Strategies

RED detects and prevents potentially misreported results. It is customary to primarily rely upon testing and code reviews as the preferred approaches for achieving a desired quality level. However, RED greatly reduces the need for code reviews, which are necessarily difficult and resource intensive exercises when testing complicated modules.

Closed Loop Checking is another strategy that incurs significant development, integration, and verification expenses. Further, closed loop checking performed within the module in question may not be reliable in all situations. Closed loop checking performed within a module is often not independent of the module being tested.

The RED architecture can accept many different types of inputs. The two obvious choices are Subsystem I/O (composed of Subsystem Commands, Responses, and Asynchronous messages) and DataLogger events.

In a preferred embodiment RED performs the requested checks and passes back a response indicating the status (pass, fail, or optionally—a warning level). RED recognizes that each assay model will have different protocol steps and therefore different integrity checks. The categories of checks associated with a replicate are listed. Each category correlates with a table of expected events that may be dynamically altered depending upon replicate protocol information. Thus, RED potentially simplifies coding for the analyzer and provides improved reliability to the results by providing a test independent of the complexity inherent in real-time handling of message traffic in an analyzer or another complex system.

Figure 5:
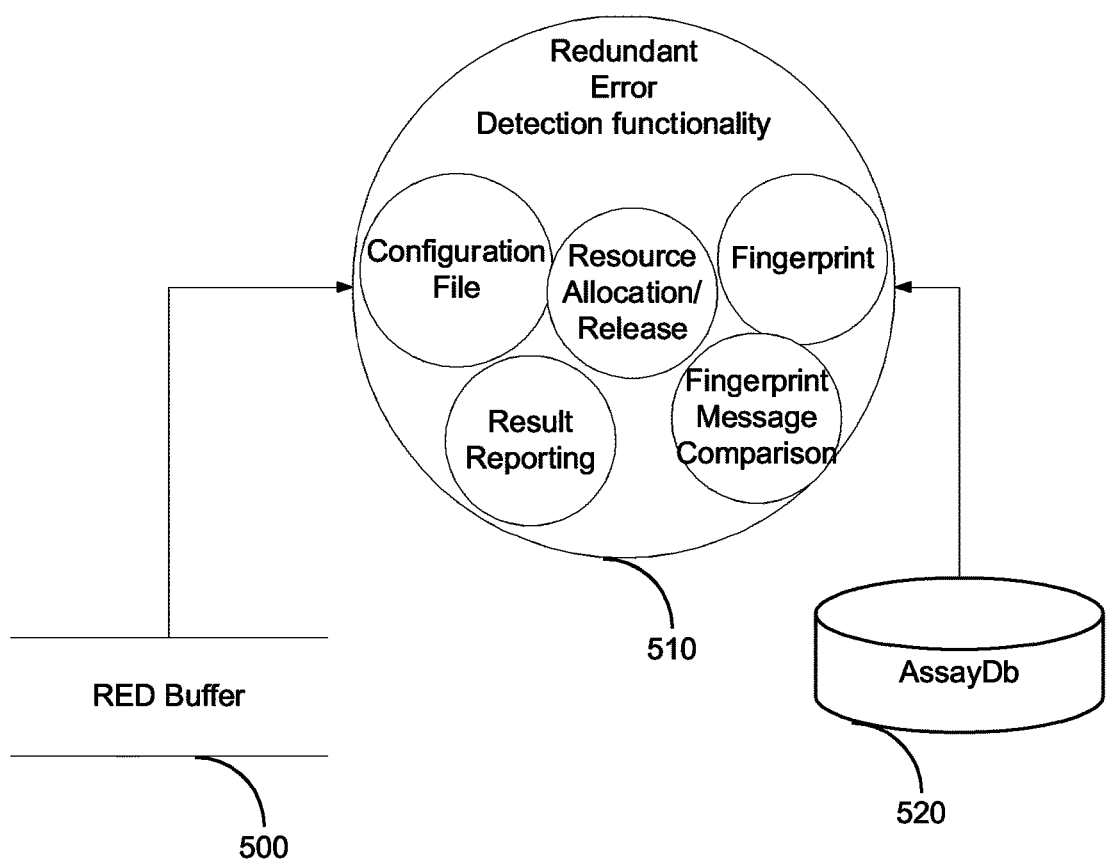
FIG. 5 illustrates a method for evaluating and debugging software using a redundant error detector.

FIG. 5 illustrates the RED functionality. Typically, there is a mechanism for transferring messages and information, here RED Buffer 500, which provides commands and data to Redundant Error Detector Functionality 510. Redundant Error Detector Functionality 510 includes, in a preferred embodiment, a configuration file, fingerprint and its generation capability, capability to compare fingerprint to messages from RED Buffer 500, result reporting capability and resource allocation and release functions. The Assay Database 520 is accessible to Redundant Error Detector Functionality 510, which access is useful for generating the fingerprints.

One skilled in the art will appreciate this disclosure is susceptible to many variations and alternative implementations without departing from its teachings or spirit. For instance, complex systems other than clinical analyzers will benefit by redundant error testing as described herein based on evaluating each output for consistency evaluated using a fingerprint of events. The scope of the claims appended below includes many such modifications. Further, each reference discussed and cited herein is hereby incorporated herein by reference in its entirety.

The invention claimed is:

1. A clinical diagnostic analyzer system with validation of a replicate measurement of a patient sample using post-measurement error detection, the clinical diagnostic analyzer system comprising:
   a patient sample input device for receiving the patient sample; and
   a processor for executing instructions to perform the steps of an analysis method using the clinical diagnostic analyzer system, the analysis method comprising:
      performing the replicate measurement of the patient sample with instructions of a required assay;
      receiving measurement messages as a result of performing the replicate measurement;
      receiving device status messages indicating status of the clinical diagnostic analyzer system;
      generating a fingerprint of expected events to be tested for the replicate measurement from at least a configuration information and a protocol information thereof, wherein the protocol information contains details for the assay required by the replicate measurement;
      validating the replicate measurement of the patient sample by comparing the received measurement and device status messages with the fingerprint to facilitate error detection, the validating step comprising the step of matching the received measurement messages and the received device status messages with the fingerprint of the expected events to determine a success or a failure of the replicate measurement; and
      releasing the replicate measurement upon the success of the replicate measurement and preventing release of the replicate measurement upon the failure of the replicate measurement.

2. The clinical diagnostic analyzer system of claim 1, wherein the receiving comprises receiving messages comprising Subsystem Commands, Command Responses, and Asynchronous messages.

3. The clinical diagnostic analyzer system of claim 1, wherein the analysis method further comprises generating the fingerprint in response to receiving a Preview command for the replicate measurement.

4. The clinical diagnostic analyzer system of claim 3, wherein the analysis method further comprises releasing all resources, which were sequestered in response to receiving the Preview command for the replicate measurement, in response to receiving a Complete command.

5. The clinical diagnostic analyzer system of claim 1, wherein the analysis method further comprises completing, in response to a Check command, a comparison of the fingerprint with received messages.

6. The clinical diagnostic analyzer system of claim 1, wherein the analysis method further comprises dynamically releasing a result of the comparison.

7. The clinical diagnostic analyzer system of claim 1, wherein the analysis method further comprises logging conditions in response to validating the replicate measurement.

8. The clinical diagnostic analyzer system of claim 1, wherein the analysis method further comprises logging conditions in response to flagging results of the assay with a warning.

9. The clinical diagnostic analyzer system of claim 1, wherein the analysis method further comprises generating events corresponding to a subsystem in response to receiving a Preview command for the replicate measurement, wherein the generation is based on the configuration information.

10. A method for validation by a clinical diagnostic analyzer system of a replicate measurement of a patient sample using post-measurement error detection, the method comprising:

receiving a preview replicate command for a replicate measurement;

allocating resources for redundant error checking for the replicate measurement;

generating a fingerprint of required events for the replicate measurement using at least a configuration information and an protocol information, wherein the fingerprint has fewer events than events performed in accordance with the protocol information for the replicate;

comparing measurement messages corresponding to carrying out the replicate measurement, and device status messages indicating status of the clinical diagnostic analyzer system, with the fingerprint, the comparing step comprising the step of matching the measurement messages and the device status messages with the generated fingerprint to determine a success or a failure of the replicate measurement;

sending a result of the comparison to facilitate releasing the replicate measurement upon the success of the replicate measurement and preventing release of the replicate measurement upon the failure of the replicate measurement; and logging conditions corresponding to the replicate measurement.

11. The method of claim 10, wherein the configuration information is coded in eXtensible Markup Language.

12. The method of claim 10, wherein logging conditions includes writing data relating to specified events to a log file in a specified format.

13. The method of claim 10, wherein the result corresponding to the replicate measurement being an error detection causes the clinical diagnostic analyzer to not release the result.

* * * * *